(12) United States Patent
Vaughn et al.

(10) Patent No.: US 11,075,007 B2
(45) Date of Patent: Jul. 27, 2021

(54) DYNAMIC SELECTION OF VIRTUAL AGENTS IN A MUTLI-DOMAIN EXPERT SYSTEM

(71) Applicant: International Business Machines Corporation, Armonk, NY (US)

(72) Inventors: Garfield Vaughn, South Windsor, CT (US); Gandhi Sivakumar, Bentleigh (AU); Vasanthi M. Gopal, Plainsboro, NJ (US)

(73) Assignee: International Business Machines Corporation, Armonk, NY (US)

( * ) Notice: Subject to any disclaimer, the term of this patent is extended or adjusted under 35 U.S.C. 154(b) by 357 days.

(21) Appl. No.: 16/038,332

(22) Filed: Jul. 18, 2018

(65) Prior Publication Data
US 2020/0027553 A1    Jan. 23, 2020

(51) Int. Cl.
| | |
|---|---|
| *G16H 50/20* | (2018.01) |
| *G06N 5/04* | (2006.01) |
| *G06N 20/00* | (2019.01) |
| *G06F 40/30* | (2020.01) |

(52) U.S. Cl.
CPC ............ *G16H 50/20* (2018.01); *G06F 40/30* (2020.01); *G06N 5/04* (2013.01); *G06N 20/00* (2019.01)

(58) Field of Classification Search
CPC .......... G16H 50/20; G06N 20/00; G06N 5/04; G06F 40/30
USPC ....................................................... 705/2–3
See application file for complete search history.

(56) References Cited

U.S. PATENT DOCUMENTS

| | | | |
|---|---|---|---|
| 2012/0265528 A1 | 10/2012 | Gruber | |
| 2014/0074454 A1* | 3/2014 | Brown | G10L 15/08 704/9 |
| 2014/0249830 A1* | 9/2014 | Gallopyn | G06F 19/00 705/2 |
| 2014/0365407 A1 | 12/2014 | Brown | |
| 2015/0142704 A1* | 5/2015 | London | G06F 40/58 706/11 |
| 2015/0186156 A1 | 7/2015 | Brown et al. | |
| 2015/0215350 A1 | 7/2015 | Slayton et al. | |

(Continued)

FOREIGN PATENT DOCUMENTS

| | | |
|---|---|---|
| EP | 2575128 A2 | 4/2013 |
| WO | WO2017161139 | 9/2017 |

*Primary Examiner* — Michael Tomaszewski
(74) *Attorney, Agent, or Firm* — Schmeiser, Olsen & Watts; Brian M. Restauro

(57) ABSTRACT

An expert system incorporates multiple virtual-agent experts, each trained in a particular field or domain. When a user enters a block of input, an interactive front-end infers the semantic meaning of the input and creates a chat-table record that stores the inferred meaning and other characteristics of the input. A distributed virtual-assistant manager (DVAM) module uses that record to identify the domain of the input and, after retrieving cross-reference information stored in a virtual-assistant intent (VAI) table, selects a virtual-agent expert trained in the identified domain. If necessary, the DVAM directs the front-end to seamlessly switch the user to the newly selected expert. As the session continues, the system continues to dynamically switch the user to different experts as the session traverses different domains. The system may also consider the domain history of the entire session when selecting a domain.

20 Claims, 5 Drawing Sheets

(56) References Cited

U.S. PATENT DOCUMENTS

2017/0076223 A1* 3/2017 Kozhaya ................ G06N 20/00
2018/0054523 A1* 2/2018 Zhang ..................... G06N 5/04

* cited by examiner

DYNAMIC SELECTION OF VIRTUAL AGENTS IN A MUTLI-DOMAIN EXPERT SYSTEM

BACKGROUND

The present invention relates in general to artificially intelligent expert systems and in particular to a multi-domain expert system comprising multiple virtual agents that are each trained to provide expertise in a particular domain.

Expert-system technology is an application of artificial intelligence in which a computer program, sometimes known as a virtual agent, emulates a human expert with expertise in a particular field (or "domain"). For example, a medical expert system might comprise a virtual doctor that interactively solicits information from a human patient, through a natural-language processing (NLP) computer interface, and uses that information to diagnose and treat the patient's ailment.

Like human experts, virtual agents gain expertise in a particular field or domain through "hands-on" experience. This is generally accomplished through a machine-learning procedure that trains a virtual agent with a large volume of user-expert interactions known as a "corpus." By inferring meaning from the corpus data, the virtual agent learns how to interact appropriately with users in the desired domain.

For example, a virtual doctor may be trained by analyzing logs of doctor-patient interactions from which the agent learns how to identify patterns of symptoms described patients' natural-language input, how to associate an underlying ailment as a function of inferred symptoms, and how to most effectively treat the diagnosed ailment.

Expert systems are today used in many domains: Virtual agents may, for example, provide technical support, help home buyers configure modular houses, assist writers with grammatical construction, prepare tax returns, troubleshoot manufacturing problems, give financial advice, or design products.

More sophisticated expert systems may comprise multiple virtual agents, each of which has been trained in a specific domain. Such systems can be effective in applications like a telecommunications carrier's support operation, where experts are required to address problems in domains as diverse as: wireless services, landline services, terminal devices and handset hardware, infrastructure, service-plan configuration, and smartphone compatibility. In such a system, a distinct set of agents would have been trained in each of these domains with a corresponding domain-specific corpus.

It is not unusual for an unstructured, natural-language user session to traverse multiple domains. However, known multi-domain expert systems can today switch a caller between virtual agents only by means of voice-menu selections, an express user-entered instruction, or a human operator's manual intervention. Extending expert-system technology to multiple-domain, multiple-agent applications therefore introduces technology-specific problems that make it difficult to conduct seamlessly transparent multi-domain sessions.

For example, a user's service call to a telecommunications carrier may, over the course of the call, require a series of virtual agents to address an evolving problem definition. The caller's problem may initially be diagnosed as a suspected smartphone incompatibility, but subsequent analysis may require expert advice from agents trained to handle smartphone-application issues and wireless-service problems, and may conclude with an expert analysis of the user's current service plan and billing configuration. In known multi-domain expert systems, such a call might require the customer to manually transfer to each virtual agent using buttons on the user's phone. This degrades the user's experience, increases call-handling complexity, and introduces the possibility of wait times and incorrect agent selection.

SUMMARY

An embodiment of the present invention is a multi-domain expert system comprising a processor, a memory coupled to the processor, and a computer-readable hardware storage device coupled to the processor, the storage device containing program code configured to be run by the processor via the memory to implement a method for dynamic selection of virtual agents in a multi-domain expert system, the method comprising:

a processor of a distributed virtual-assistant manager (DVAM) receiving notice that a user has initiated a user session, where the expert system comprises the DVAM, a front-end program that interacts with the user, a chat table, a virtual agent intent (VAI) table, and a set of pretrained virtual agents;

the processor receiving a communication from the front-end program that a first block of input has been received from the user by the front-end program;

the processor retrieving a first chat-table record from the chat table, where the first chat-table record identifies a first semantic meaning of the first block of input;

the processor associating, as a function of the first semantic meaning, the first block of input with a first domain of a set of predefined domains;

the processor selecting a first virtual agent from the set of pretrained virtual agents, where the first virtual agent possesses expert knowledge in the first domain; and the processor directing the front-end program to conduct the user session as an interactive conversation between the user and the first virtual agent.

Another embodiment of the present invention is a method for dynamic selection of virtual agents in a multi-domain expert system, the method comprising:

a processor of a distributed virtual-assistant manager (DVAM) module receiving notice that a user has initiated a user session, where the multi-domain expert system comprises the DVAM, a front-end program that interacts with the user, a chat table, a virtual agent intent (VAI) table, and a set of pretrained virtual agents;

the processor receiving a communication from the front-end program that a first block of input has been received from the user by the front-end program;

the processor retrieving a first chat-table record from the chat table, where the first chat-table record identifies a first semantic meaning of the first block of input;

the processor associating, as a function of the first semantic meaning, the first block of input with a first domain of a set of predefined domains;

the processor selecting a first virtual agent from the set of pretrained virtual agents, where the first virtual agent possesses expert knowledge in the first domain; and the processor directing the front-end program to conduct the user session as an interactive conversation between the user and the first virtual agent.

Yet another embodiment of the present invention is a computer program product, comprising a computer-readable hardware storage device having a computer-readable program code stored therein, the program code configured to be executed by a multi-domain expert system comprising a processor, a memory coupled to the processor, and a computer-readable hardware storage device coupled to the processor, the storage device containing program code configured to be run by the processor via the memory to implement a method for dynamic selection of virtual agents in a multi-domain expert system, the method comprising:

a processor of a distributed virtual-assistant manager (DVAM) module receiving notice that a user has initiated a user session, where the multi-domain expert system comprises the DVAM, a front-end program that interacts with the user, a chat table, a virtual agent intent (VAI) table, and a set of pretrained virtual agents;

the processor receiving a communication from the front-end program that a first block of input has been received from the user by the front-end program;

the processor retrieving a first chat-table record from the chat table, where the first chat-table record identifies a first semantic meaning of the first block of input;

the processor associating, as a function of the first semantic meaning, the first block of input with a first domain of a set of predefined domains;

the processor selecting a first virtual agent from the set of pretrained virtual agents, where the first virtual agent possesses expert knowledge in the first domain; and the processor directing the front-end program to conduct the user session as an interactive conversation between the user and the first virtual agent.

DETAILED DESCRIPTION

Figure 1:
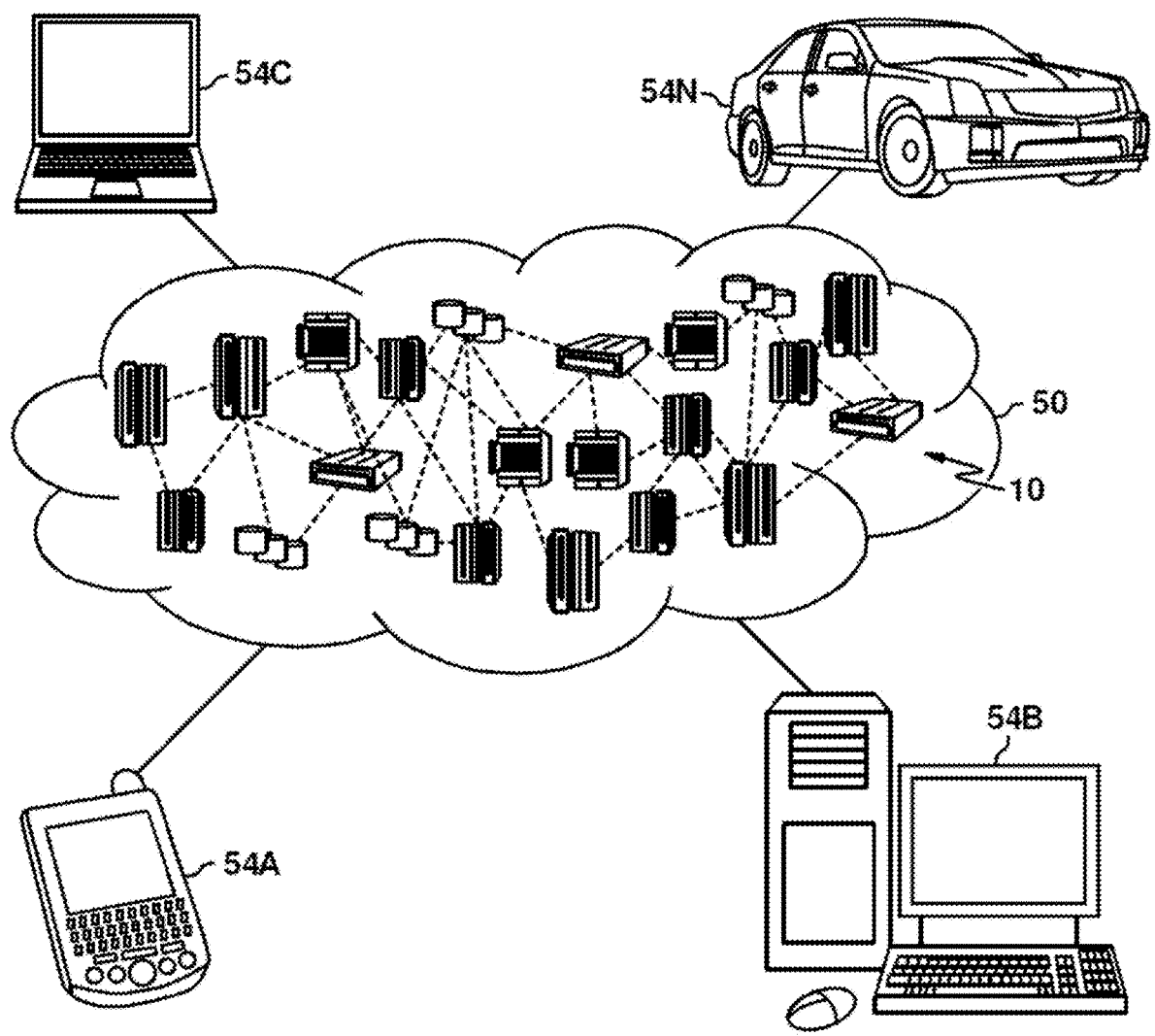
FIG. 1 depicts a cloud computing environment according to an embodiment of the present invention.

Expert-system technology is an application of artificial intelligence in which a computer program, sometimes known as a virtual agent, emulates a human expert with expertise in a particular field (or "domain").

Expert systems are today used to provide human-like expert advice in many types of applications. Virtual agents may, for example, provide technical support to customers of a software company, help home buyers configure modular houses, assist writers with grammatical construction, prepare tax returns, troubleshoot manufacturing problems, give financial advice, or design products.

More sophisticated expert systems may comprise multiple virtual agents, each of which has been trained in a specific domain. Such systems multi-agent systems could, for example, be comprised by:

a telecommunications carrier's support operation, where experts are required to address problems in domains as diverse as: wireless services, landline services, terminal devices and handset hardware, infrastructure, service-plan configuration, and smartphone compatibility;

a 911 emergency-response service, in which virtual agents are trained to expertly identify and rank reported emergencies and to quickly determine an appropriate course of action;

a telemedicine service at a hospital or clinic, where each expert has been trained to have expertise with a particular class of medical issues or in a particular medical specialty; or a law firm or legal service in which each expert has expertise in a different field of law or with a particular type of client or type of legal action.

In such systems, a distinct set of agents may each be trained in a particular domain with a corresponding domain-specific corpus.

Known multi-domain expert systems can switch a caller between virtual agents only by means of a voice-menu selection, an express user-entered instruction, or a human operator's manual intervention. Extending expert-system technology to multiple-domain, multiple-agent natural-language applications therefore introduces a technology-specific problem that makes it difficult to conduct efficient, user-friendly, and seamlessly transparent multi-domain sessions.

Embodiments of the present invention provide a technical solution to this technical problem by adding novel components to a multi-agent expert system. An interactive front-end connects a user to appropriate virtual agents that are selected by a distributed virtual-assistant manager (DVAM), based on dynamic analysis of the user's input. The front-end extracts semantic meaning from each user statement and stores that meaning (along with other characteristics of the user statement) as a record of a chat table.

The DVAM uses the chat-table record to dynamically identify the domain of the user input and then uses an agent/domain cross-reference stored in a virtual-agent intent (VAI) table to identify which virtual agent should respond to the input. The DVAM then seamlessly switches control of the conversation to the newly identified virtual agent and directs the front-end to seamlessly continue the conversational user session with the new virtual agent.

Embodiments of this method improve existing multi-agent expert systems by providing this seamless user experience. They also scale up easily to implementations that comprise a large number of domains virtual experts by providing the dedicated DVAM agent-selection mechanism, which decouples the interactive user interface from the expert agents, even if those agents reside on different networks or are implemented on different platforms.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are aVAIlable over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application posting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
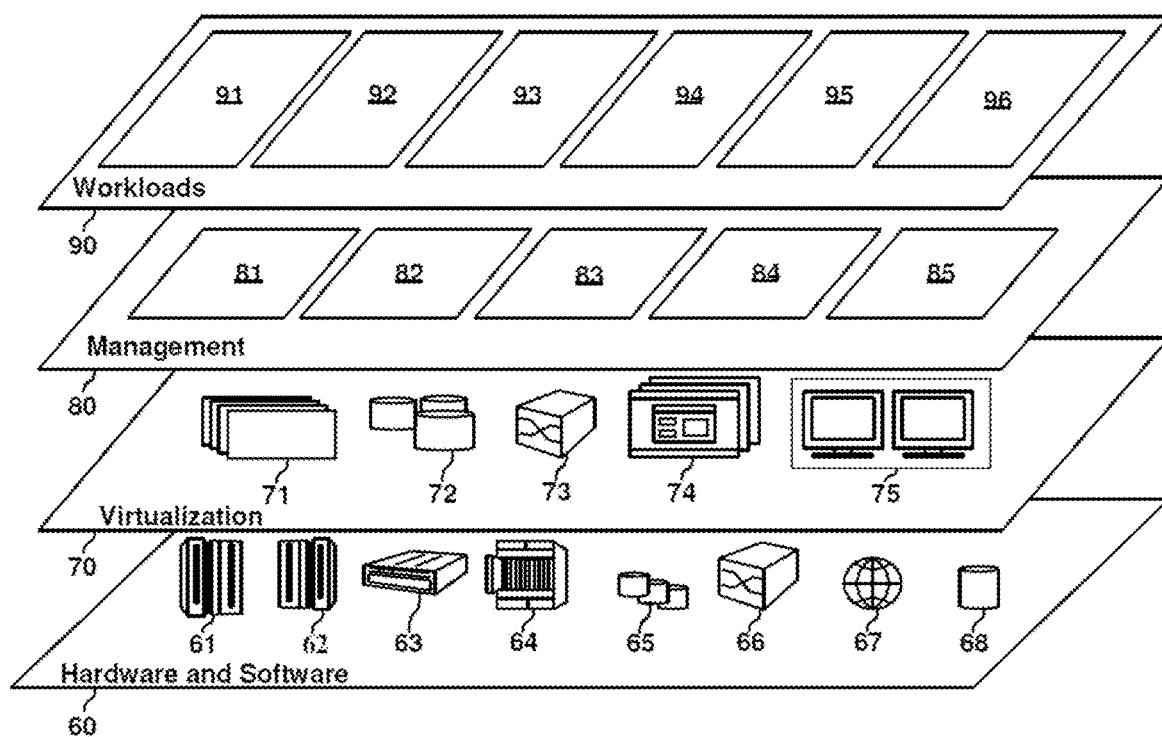
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and orchestration of dynamic selection of virtual agents in a multi-domain expert system.

Aspects of the present invention may take the form of an entirely hardware embodiment, an entirely software embodiment (including firmware, resident software, micro-code, etc.) or embodiment combining software and hardware aspects that may all generally be referred to herein as a "circuit," "module," or "system."

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer-readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 3:
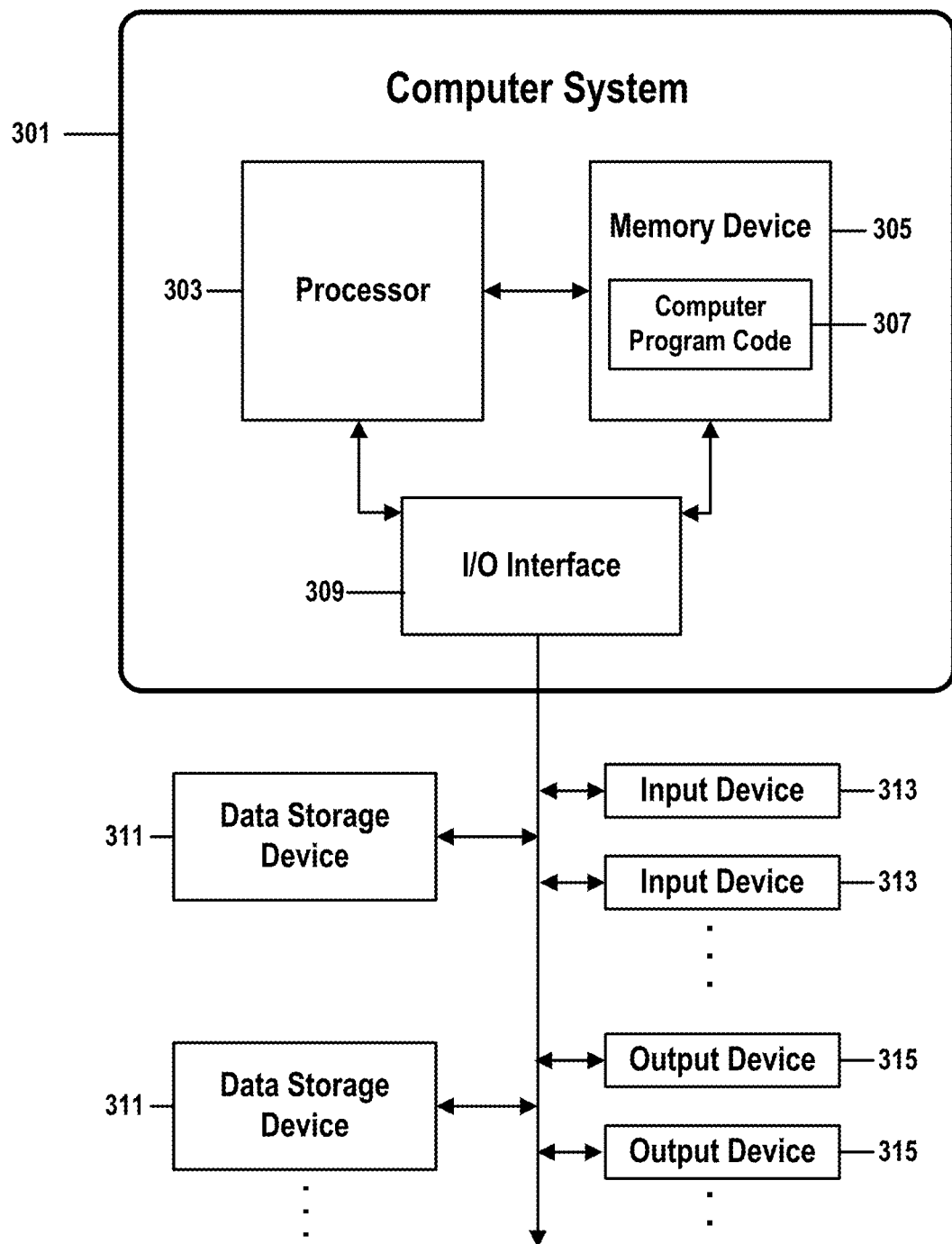
FIG. 3 shows the structure of a computer system and computer program code that may be used to implement a method for dynamic selection of virtual agents in a multi-domain expert system accordance with embodiments of the present invention.

FIG. 3 shows a structure of a computer system and computer program code that may be used to implement a method for dynamic selection of virtual agents in a multi-domain expert system in accordance with embodiments of the present invention, FIG. 3 refers to objects 301-315.

In FIG. 3, computer system 301 comprises a processor 303 coupled through one or more I/O Interfaces 309 to one or more hardware data storage devices 311 and one or more I/O devices 313 and 315.

Hardware data storage devices 311 may include, but are not limited to, magnetic tape drives, fixed or removable hard disks, optical discs, storage-equipped mobile devices, and solid-state random-access or read-only storage devices. I/O devices may comprise, but are not limited to: input devices 313, such as keyboards, scanners, handheld telecommunications devices, touch-sensitive displays, tablets, biometric readers, joysticks, trackball's, or computer mice; and output devices 315, which may comprise, but are not limited to printers, plotters, tablets, mobile telephones, displays, or sound-producing devices. Data storage devices 311, input devices 313, and output devices 315 may be located either locally or at remote sites from which they are connected to I/O Interface 309 through a network interface.

Processor 303 may also be connected to one or more memory devices 305, which may include, but are not limited to, Dynamic RAM (DRAM), Static RAM (SRAM), Programmable Read-Only Memory (PROM), Field-Programmable Gate Arrays (FPGA), Secure Digital memory cards, SIM cards, or other types of memory devices.

At least one memory device 305 contains stored computer program code 307, which is a computer program that comprises computer-executable instructions. The stored computer program code includes a program that implements a method for dynamic selection of virtual agents in a multi-domain expert system in accordance with embodiments of the present invention, and may implement other embodiments described in this specification, including the methods illustrated in FIGS. 1-5. The data storage devices 311 may store the computer program code 307. Computer program code 307 stored in the storage devices 311 is configured to be executed by processor 303 via the memory devices 305. Processor 303 executes the stored computer program code 307.

In some embodiments, rather than being stored and accessed from a hard drive, optical disc or other writeable, rewriteable, or removable hardware data-storage device 311, stored computer program code 307 may be stored on a static, nonremovable, read-only storage medium such as a Read-Only Memory (ROM) device 305, or may be accessed by processor 303 directly from such a static, nonremovable, read-only medium 305. Similarly, in some embodiments, stored computer program code 307 may be stored as computer-readable firmware 305, or may be accessed by processor 303 directly from such firmware 305, rather than from a more dynamic or removable hardware data-storage device 311, such as a hard drive or optical disc.

Thus the present invention discloses a process for supporting computer infrastructure, integrating, hosting, maintaining, and deploying computer-readable code into the computer system 301, wherein the code in combination with the computer system 301 is capable of performing a method for dynamic selection of virtual agents in a multi-domain expert system.

Any of the components of the present invention could be created, integrated, hosted, maintained, deployed, managed, serviced, supported, etc. by a service provider who offers to facilitate a method for dynamic selection of virtual agents in a multi-domain expert system Thus the present invention discloses a process for deploying or integrating computing infrastructure, comprising integrating computer-readable code into the computer system 301, wherein the code in combination with the computer system 301 is capable of performing a method for dynamic selection of virtual agents in a multi-domain expert system.

One or more data storage units 311 (or one or more additional memory devices not shown in FIG. 3) may be used as a computer-readable hardware storage device having a computer-readable program embodied therein and/or having other data stored therein, wherein the computer-readable program comprises stored computer program code 307. Generally, a computer program product (or, alternatively, an article of manufacture) of computer system 301 may comprise the computer-readable hardware storage device.

In embodiments that comprise components of a networked computing infrastructure, a cloud-computing environment, a client-server architecture, or other types of distributed platforms, functionality of the present invention may be implemented solely on a client or user device, may be implemented solely on a remote server or as a service of a cloud-computing platform, or may be split between local and remote components.

While it is understood that program code 307 for a method for dynamic selection of virtual agents in a multi-domain expert system may be deployed by manually loading the program code 307 directly into client, server, and proxy computers (not shown) by loading the program code 307 into a computer-readable storage medium (e.g., computer data storage device 311), program code 307 may also be automatically or semi-automatically deployed into computer system 301 by sending program code 307 to a central server-computer system 301) or to a group of central servers. Program code 307 may then be downloaded into client computers (not shown) that will execute program code 307.

Alternatively, program code 307 may be sent directly to the client computer via e-mail. Program code 307 may then either be detached to a directory on the client computer or loaded into a directory on the client computer by an e-mail option that selects a program that detaches program code 307 into the directory.

Another alternative is to send program code 307 directly to a directory on the client computer hard drive. If proxy servers are configured, the process selects the proxy server code, determines on which computers to place the proxy servers' code, transmits the proxy server code, and then installs the proxy server code on the proxy computer. Program code 307 is then transmitted to the proxy server and stored on the proxy server.

In one embodiment, program code 307 for a method for dynamic selection of virtual agents in a multi-domain expert system is integrated into a client, server and network environment by providing for program code 307 to coexist with software applications (not shown), operating systems (not shown) and network operating systems software (not shown) and then installing program code 307 on the clients and servers in the environment where program code 307 will function.

The first step of the aforementioned integration of code included in program code 307 is to identify any software on the clients and servers, including the network operating system (not shown), where program code 307 will be deployed that are required by program code 307 or that work in conjunction with program code 307. This identified software includes the network operating system, where the network operating system comprises software that enhances a basic operating system by adding networking features. Next, the software applications and version numbers are identified and compared to a list of software applications and correct version numbers that have been tested to work with program code 307. A software application that is missing or that does not match a correct version number is upgraded to the correct version.

A program instruction that passes parameters from program code 307 to a software application is checked to ensure that the instruction's parameter list matches a parameter list required by the program code 307. Conversely, a parameter passed by the software application to program code 307 is checked to ensure that the parameter matches a parameter required by program code 307. The client and server operating systems, including the network operating systems, are identified and compared to a list of operating systems, version numbers, and network software programs that have been tested to work with program code 307. An operating system, version number, or network software program that does not match an entry of the list of tested operating systems and version numbers is upgraded to the listed level on the client computers and upgraded to the listed level on the server computers.

After ensuring that the software, where program code 307 is to be deployed, is at a correct version level that has been tested to work with program code 307, the integration is completed by installing program code 307 on the clients and servers.

Embodiments of the present invention may be implemented as a method performed by a processor of a computer system, as a computer program product, as a computer system, or as a processor-performed process or service for supporting computer infrastructure.

Figure 4:
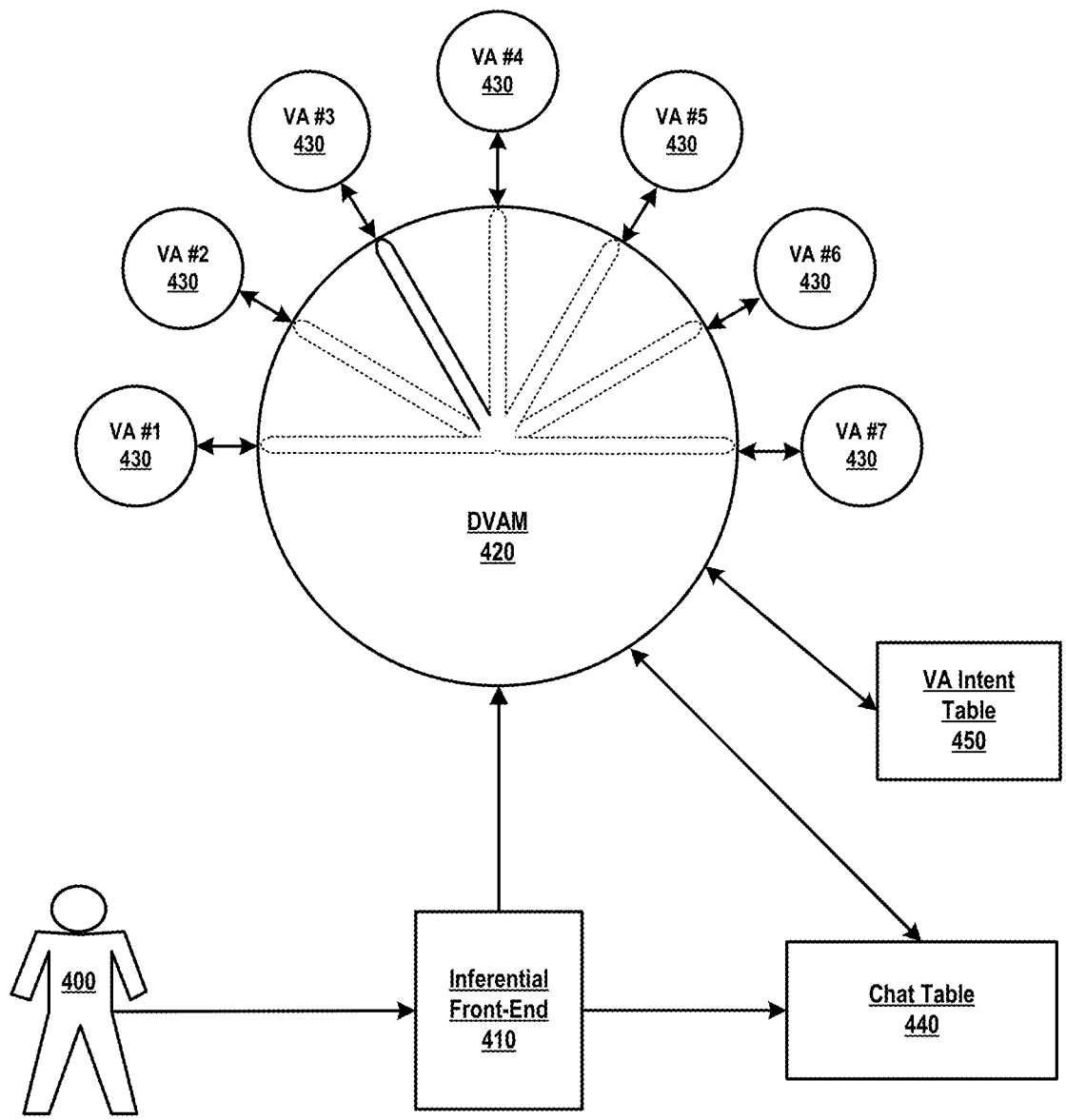
FIG. 4 shows an architecture of an improved multi-domain expert system that dynamically selects virtual agents in accordance with embodiments of the present invention.

FIG. 4 depicts an architecture of an improved multi-domain expert system that dynamically selects virtual agents in accordance with embodiments of the present invention. FIG. 4 shows elements 400-450.

In this figure, a user 400 communicates with the expert system through an inferential user interface 410, such as a natural-language processing (NLP) front-end or other cognitive or artificially intelligent interface capable to inferring meaning to natural-language user input.

In some embodiments, this cognitive front-end 400 may be replaced by a simple token-based or other type of parsing, finite-state machine, or other non-cognitive interface. In such cases, user 400 would communicate with the system through a structured mechanism, such as by entering data into a form or by selecting options from a menu.

The front-end 400 transfers data to a chat table 440 that stores data related to the current user session. Although the exact format of chat table 440 may be implementation-dependent, in one example, each record of the table might comprise fields that record a session identifier, a date or time tag, a block of user input, an inferred meaning or intent of the block of input, and an identifier of an expert virtual assistant 430 that will bit responsible for responding to the block of input.

Virtual agent intent (VAI) table 450 is a cross-reference that identifies a domain of expertise in which each virtual agent 430 has been trained.

The front-end 410 and chat table 440 also communicate with distributed virtual-assistant manager (DVAM) module 420, which maintains rules for selecting which virtual agent 430 should communicate with user 400.

For example, if the front-end 410 infers from a block of user input, or from historic information stored in chat table 440, that the user is seeking help with a certain type of infection, front-end 410 would store that information in a chat table record and would request that DVAM 420 switch control to an appropriate virtual agent of the group of agents 430. DVAM 420 might then, by reading information in the chat table 440, or by receiving information received from the front-end 410, select a virtual agent 430 that is identified in VAI table 450 as having been trained in diagnosing and treating the desired type of infection. From this point on, the selected virtual agent 430 would communicate with user 400 through the front-end 410. If a subsequent block of user input indicates that the user has switched to a different topic, the process would be repeated in order to switch control to a different agent 430.

Embodiments of the present invention are flexible enough to accommodate variations of this architecture, if desired by an implementer. For example, VAI table 450 may interface directly with chat table 440, enabling each record of the chat table 440 to identify to DVAM 420 a particular virtual assistant 430.

Figure 5:
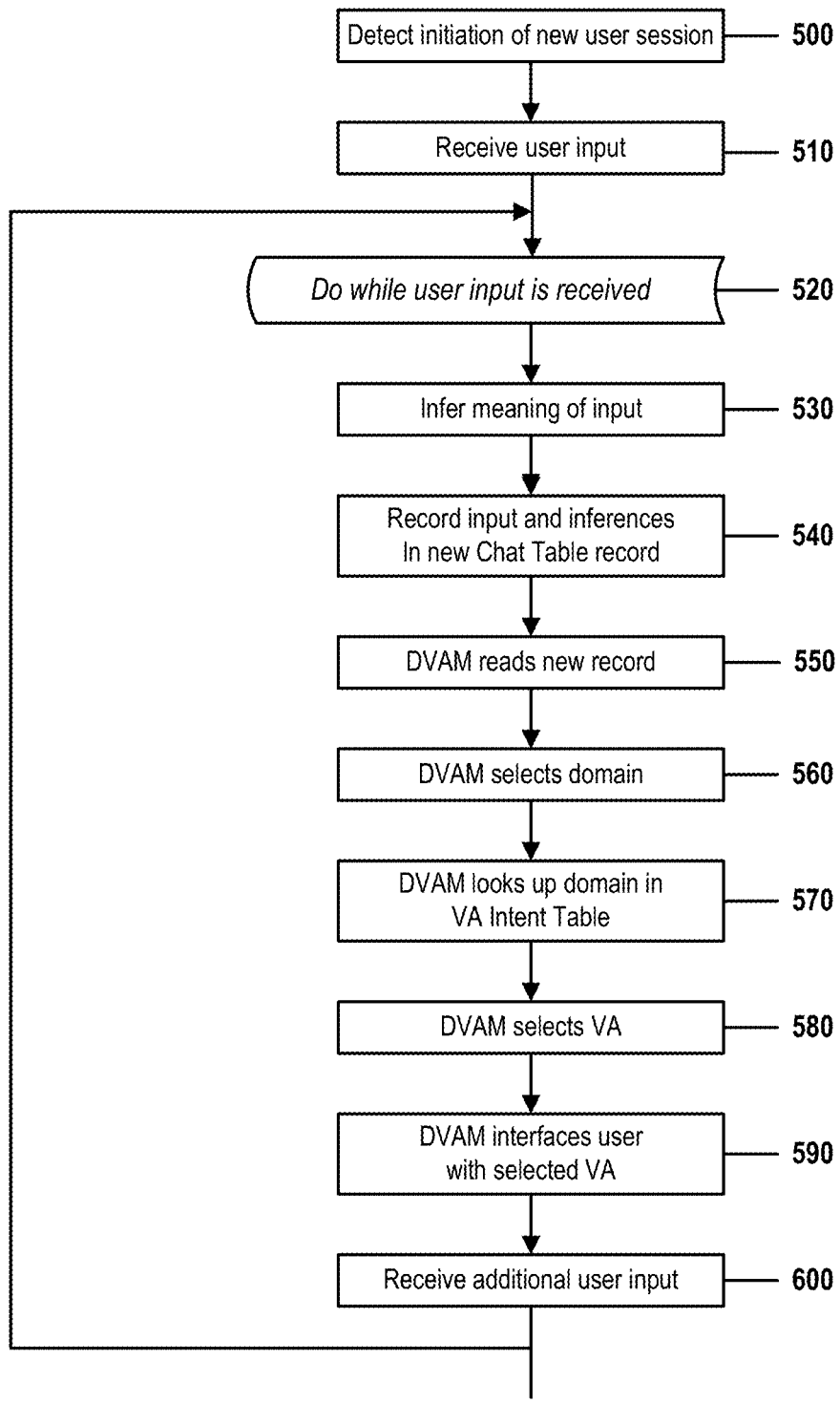
FIG. 5 is a flow chart that illustrates steps of a method for dynamic selection of virtual agents by a multi-domain expert system accordance with embodiments of the present invention.

FIG. 5 is a flow chart that illustrates steps of a method for dynamic selection of virtual agents by a multi-domain expert system in accordance with embodiments of the present invention. FIG. 5 shows steps 500-600.

In step 500, a distributed expert system detects that a user 400 has initiated a session. This detection may be made by any means known in the art. For example, a computerized telephone system, a hosted cloud service, or a network interface may notify the expert system that a user has made a voice call into a help center or has initiated a real-time textual Web chat.

In step 510, the system receives a block of input from user 400 through a user interface 410. If the input is structured, such as data entered into a form or selections made from menus, user interface may be able to infer meaning from the input without requiting cognitive functionality. If, however, the input is unstructured or natural-language input, the interface 410 may be an NLP module or other type of artificially intelligent or cognitive interface capable of inferring meaning from natural-language input or from context of the input.

Step 520 begins the iterative procedure of steps 520-600, which is performed once for each block of input received from user 400. Each iterative of this iterative procedure selects, as a function of the received input, a virtual agent 430 that has been trained in a domain most appropriate to the received input.

In step 530, the expert system infers meaning to the most recently received block of input. This inference may be performed by any method known in the art. Front end 410, for example, may use known methods of natural-language processing (NLP) to extract meaning from natural-language text typed by a user 400 during a live chat session. If user 400 is conversing with the interface on a telephone call, an NLP module may, by known means, receive a textual transcript of each line of conversation from a text-to-speech application. In some or all of the input is structured, such as through a user's completion of forms or interface with an interactive "wizard" interface, the front-end 410 may infer meaning by means of known parsing, pattern-matching, keyword-matching, or finite-state methods.

In step 540, the front-end (or a similar component of the expert system) populates chat table 440 with a record that characterizes the received input. This record may be formatted in any manner desired by an implementer, but should always at least comprise fields that identify; the current session, the block of input being processed, the meaning or context of the input block of text inferred in step 530, and a time stamp. In some embodiments, each record of the chat table 440 may also store the input block of text, which may be used for subsequent analysis. In other embodiments, the input block of text may be stored in another table that is distinct from chat table 440

Each record may also include a field capable of identifying a virtual assistant 430 that has been trained to address issues in the particular domain identified by the inferred meaning or context; or may also include a field that identifies a domain associated with that virtual assistant 430. In such embodiments, one or both of these fields may be filled out by DVAM 420 in step 580.

In certain embodiments, steps 530 and 540 may be performed all or in part by DVAM 420. In such embodiments, the functionality of DVAM 420 is expanded to include the ability to infer semantic meaning of an input block, and DVAM 420 may then store the inferred meaning in the chat table.

In step 550, WANT 420 retrieves the new record of chat table 440 that was created in step 540. This step may be performed in response to a notification received by DVAM 420, from front-end 410 or from chat table 440, that the new record has been created.

In step 560, DVAM 420 associates a domain with the block of input. This association may be performed through any cognitive or non-cognitive method known in the art. For example, DVAM 420 may base this association on the presence of keywords or certain phrases in the input text or in the semantic meaning of the text inferred in step 530, or may employ known methods of artificial intelligence or semantic analytics to identify a context of the input text or the inferred meaning.

In some embodiments, DVAM 420 may in this step make more accurate identifications of the domain by considering more than one record of chat table 440. This functionality allows the expert system to, for example, identify and properly address sessions in which a user statement could be interpreted, depending on context, as being associated with different domains. In such cases, the chat-table 440 may be thought of as acting as a type of log that tracks and records each session's domain history. Such logs may also be used by other applications, such as an online analytics application, to provide non-reality e analysis of previous user sessions and of the overall accuracy of the expert system.

For example, consider the case where records of the chat table 440 indicate that user 400 has, during the current session, repeatedly alternated between issues associated with the domain "wireless service technical support" and issues associated with the domain "wireless service billing configuration." If an ambiguous phrase in the current input block makes it unclear whether DVAM 420 should in step 560 associate the current input block with domain "wireless service billing configuration" or "smartphone purchase options," then DVAM 420 would be more likely to select the former domain because that domain has been more often associated with the current session.

In a more nuanced example, the current session may have so far consisted of lengthy discussions in the domain "wireless service technical support" and single comments in the domain "wireless service billing configuration." If the current input block could be associated with either domain "wireless service billing configuration" or domain "wireless service billing configuration," DVAM 420 might resolve the problem by referring to earlier records of the current session. If the three records immediately preceding the current record are, chronologically, associated with domains "wireless service billing configuration," "wireless service billing configuration," and "wireless service technical support," DVAM 420 might infer that the current input is likely in domain "wireless service technical support," because user 400, when conversing in this domain, has characteristically remained in that domain through multiple records.

If DVAM 420 determines in this step that the domain of the current block of input is identical to the domain of the immediately preceding block, then there is no need to perform steps 570-590 and the current iteration of the iterative procedure of steps 520-600 continues with step 600.

In step 570, DVAM 420 determines which virtual agent 430 possesses expertise in the domain identified in step 560. This determination is performed by means of a simple lookup into the VAI table 450, which cross-references domains and virtual agents.

In step 580, DVAM 420 selects the virtual agent 430 identified in step 590. This selected agent 430 will respond to the user input and will begin handling the user session until an iteration of the iterative procedure of steps 520-600 determines that the domain of the user's input has changed.

In some embodiments, DVAM 420 will record the selected domain or record an identifier of the selected virtual agent 430 in the current record of the chat table 440. As explained above, DVAM 420 may, in future iterations of step 560, use this information to more accurately select a domain of a future block of user input.

In step 590, DVAM 420 transparently resumes the user's interactive session, this time connecting user 400, through front-end 410, to the virtual agent selected in step 580. Even if this iteration of the iterative procedure of steps 520-600 requires switching the user session to a different agent 430, this process will in some embodiments be invisible to the user 400. In such embodiments, user 400 may have no indication that the session is now being controlled by a different virtual agent 430, one that has undergone training with a corpus in a different domain. The interactive user session now continues as before, with a virtual agent 430 that has expertise in the domain associated with the most recently received user input.

In step 600, the front-end user-interface 410 receives another block of user input. This receipt restarts the iterative procedure of steps 520-600, which begin processing the newly received input in order to associate that input with a domain and to then determine which virtual agent 430 should be selected in order to address issues now raised in that domain.

In one example, a user 400 may in step 510 speak or type the phrase, "The display on my smartphone is cracked." Front-end 410 may in step 530 use a method of text analytics or semantic analytics to infer that the user 400 is likely to require repair of a hardware component and then in step 540 record this inference in a new record of chat table 440. In steps 550 and 560, DVAM 420 reads the new record and determines that the issue raised by user 400 should be addressed in the domain "hardware technical support." If user 400 has entered the model of the smartphone in a pre-session form or drop-down menu, DVAM 420 might select a domain that is even more narrowly defined to identify hardware support for the user's particular model.

In this example, DVAM 420 in steps 570-590 then performs a look-up in VAI table 450 to identify which virtual agent 430 has been trained in the selected domain, optionally records the selected agent or the selected domain in the current record of chat table 440, and directs front-end 410 to continue the user session with the newly selected virtual agent 430.

Examples and embodiments of the present invention described in this document have been presented for illustrative purposes. They should not be construed to be exhaustive nor to limit embodiments of the present invention to the examples and embodiments described here. Many other modifications and variations of the present invention that do not depart from the scope and spirit of these examples and embodiments will be apparent to those possessed of ordinary skill in the art. The terminology used in this document was chosen to best explain the principles underlying these examples and embodiments, in order to illustrate practical applications and technical improvements of the present invention over known technologies and products, and to enable readers of ordinary skill in the art to better understand the examples and embodiments disclosed here.

What is claimed is:

1. A multi-domain expert system comprising a processor, a memory coupled to the processor, and a computer-readable hardware storage device coupled to the processor, the storage device containing program code configured to be run by the processor via the memory to implement a method for dynamic selection of virtual agents in a multi-domain expert system, the method comprising:

a processor of a distributed virtual-assistant manager (DVAM) receiving notice that a user has initiated a user session, where the expert system comprises the DVAM, a front-end program that interacts with the user, a chat table, a virtual agent intent (VAI) table, and a set of pretrained virtual agents;

the processor receiving a communication from the front-end program that a first block of input has been received from the user, as part of an interactive user conversation between the user and the expert system, by the front-end program;

the processor retrieving a first chat-table record from the chat table, where the first chat-table record identifies a first semantic meaning of the first block of input and where the processor chooses the first chat-table record over an other chat-table record that identifies a different semantic meaning of the first block of input at least in part because the user's previous interactive conversations, with the expert system, that were related to the first semantic meaning were on average lengthier than the user's previous interactive conversations, with the expert system, that were related to the different semantic meaning;

the processor associating, as a function of the first semantic meaning, the first block of input with a first domain of a set of predefined domains;

the processor selecting a first virtual agent from the set of pretrained virtual agents, where the first virtual agent possesses expert knowledge in the first domain;

the processor directing the front-end program to conduct the user session as an interactive conversation between the user and the first virtual agent.

2. The system of claim 1, further comprising:

the processor receiving further notice that a second block of input has been received from the user by the front-end program;

the processor retrieving a second chat-table record from the chat table, where the second chat-table record identifies a second semantic meaning of the second block of input;

the processor associating, as a function of the second semantic meaning, the second block of input with a second domain of the set of predefined domains;

the processor selecting a second virtual agent from the set of pretrained virtual agents, where the second virtual agent has been trained to possess expert knowledge in the second domain; and the processor directing the front-end program to continue the user session as an interactive conversation between the user and the second virtual agent.

3. The system of claim 2, where the front-end program continues the user session without interruption as an interactive conversation between the user and the second virtual agent, and where the continuing does not reveal to the user that the user is no longer interacting with the first virtual agent.

4. The system of claim 1, where the associating further comprises:

the processor retrieving a first VAI record from a virtual agent intent (VAI) table, and where the first VAI record identifies that the first virtual agent has been trained to possess expert knowledge in the first domain.

5. The system of claim 1, where the processor also considers records of the chat table other than the first chat-table record when associating the first block of input with the first domain.

6. The system of claim 1, where the front-end program comprises a natural-language processing technology configured to infer semantic meaning from natural-language user input submitted to the expert system through the front-end program, where the first block of input comprises natural-language text or speech, where the first chat-table record was created by the front-end program upon receipt by the front-end program of the first block of input, and where the first chat-table record identifies characteristics of the first block of input.

7. The system of claim 6, where the characteristics of the first block of input comprise:

an identifier of the user session, a time stamp that identifies when the first block of input was received, and the first semantic meaning.

8. A method for dynamic selection of virtual agents in a multi-domain expert system, the method comprising:

a processor of a distributed virtual-assistant manager (DVAM) module receiving notice that a user has initiated a user session, where the multi-domain expert system comprises the DVAM, a front-end program that interacts with the user, a chat table, a virtual agent intent (VAI) table, and a set of pretrained virtual agents;

the processor receiving a communication from the front-end program that a first block of input has been received from the user, as part of an interactive user conversation between the user and the expert system, by the front-end program;

the processor retrieving a first chat-table record from the chat table,
where the first chat-table record identifies a first semantic meaning of the first block of input and
where the processor chooses the first chat-table record over an other chat-table record that identifies a different semantic meaning of the first block of input at least in part because the user's previous interactive conversations, with the expert system, that were related to the first semantic meaning were on average lengthier than the user's previous interactive conversations, with the expert system, that were related to the different semantic meaning;

the processor associating, as a function of the first semantic meaning, the first block of input with a first domain of a set of predefined domains;

the processor selecting a first virtual agent from the set of pretrained virtual agents, where the first virtual agent possesses expert knowledge in the first domain; and the processor directing the front-end program to conduct the user session as an interactive conversation between the user and the first virtual agent.

9. The method of claim 8, further comprising:

the processor receiving further notice that a second block of input has been received from the user by the front-end program;

the processor retrieving a second chat-table record from the chat table, where the second chat-table record identifies a second semantic meaning of the second block of input;

the processor associating, as a function of the second semantic meaning, the second block of input with a second domain of the set of predefined domains;

the processor selecting a second virtual agent from the set of pretrained virtual agents, where the second virtual agent has been trained to possess expert knowledge in the second domain; and the processor directing the front-end program to continue the user session as an interactive conversation between the user and the second virtual agent.

10. The method of claim 9, where the front-end program continues the user session without interruption as an interactive conversation between the user and the second virtual agent, and where the continuing does not reveal to the user that the user is no longer interacting with the first virtual agent.

11. The method of claim 8, where the associating further comprises:

the processor retrieving a first VAI record from a virtual agent intent (VAI) table, and where the first VAI record identifies that the first virtual agent has been trained to possess expert knowledge in the first domain.

12. The method of claim 8, where the processor also considers records of the chat table other than the first chat-table record when associating the first block of input with the first domain.

13. The method of claim 8, where the front-end program comprises a natural-language processing technology configured to infer semantic meaning from natural-language user input submitted to the expert system through the front-end program, where the first block of input comprises natural-language text or speech, where the first chat-table record was created by the front-end program upon receipt by the front-end program of the first block of input, where the first chat-table record identifies characteristics of the first block of input, and where the characteristics comprise:
an identifier of the user session,
a time stamp that identifies when the first block of input was received, and
the first semantic meaning.

14. The method of claim 8, further comprising providing at least one support service for at least one of creating, integrating, hosting, maintaining, and deploying computer-readable program code in the computer system, wherein the computer-readable program code in combination with the computer system is configured to implement the receiving notice, the receiving a communication, the retrieving, the associating, the selecting, and the directing.

15. A computer program product, comprising a computer-readable hardware storage device having a computer-readable program code stored therein, the program code configured to be executed by a multi-domain expert system comprising a processor, a memory coupled to the processor, and a computer-readable hardware storage device coupled to the processor, the storage device containing program code configured to be run by the processor via the memory to implement a method for dynamic selection of virtual agents in a multi-domain expert system, the method comprising:

a processor of a distributed virtual-assistant manager (DVAM) module receiving notice that a user has initiated a user session, where the multi-domain expert system comprises the DVAM, a front-end program that interacts with the user, a chat table, a virtual agent intent (VAI) table, and a set of pretrained virtual agents;

the processor receiving a communication from the front-end program that a first block of input has been received from the user, as part of an interactive user conversation between the user and the expert system, by the front-end program;

the processor retrieving a first chat-table record from the chat table,
where the first chat-table record identifies a first semantic meaning of the first block of input and
where the processor chooses the first chat-table record over an other chat-table record that identifies a different semantic meaning of the first block of input at least in part because the user's previous interactive conversations, with the expert system, that were related to the first semantic meaning were on average lengthier than the user's previous interactive conversations, with the expert system, that were related to the different semantic meaning;

the processor associating, as a function of the first semantic meaning, the first block of input with a first domain of a set of predefined domains;

the processor selecting a first virtual agent from the set of pretrained virtual agents, where the first virtual agent possesses expert knowledge in the first domain; and the processor directing the front-end program to conduct the user session as an interactive conversation between the user and the first virtual agent.

16. The computer program product of claim 15, further comprising:

the processor receiving further notice that a second block of input has been received from the user by the front-end program;

the processor retrieving a second chat-table record from the chat table, where the second chat-table record identifies a second semantic meaning of the second block of input;

the processor associating, as a function of the second semantic meaning, the second block of input with a second domain of the set of predefined domains;

the processor selecting a second virtual agent from the set of pretrained virtual agents, where the second virtual agent has been trained to possess expert knowledge in the second domain; and the processor directing the front-end program to continue the user session as an interactive conversation between the user and the second virtual agent.

17. The computer program product of claim 16, where the front-end program continues the user session without interruption as an interactive conversation between the user and the second virtual agent, and where the continuing does not reveal to the user that the user is no longer interacting with the first virtual agent.

18. The computer program product of claim 15, where the associating further comprises:

the processor retrieving a first VAI record from a virtual agent intent (VAI) table, and where the first VAI record identifies that the first virtual agent has been trained to possess expert knowledge in the first domain.

19. The computer program product of claim 15, where the processor also considers records of the chat table other than the first chat-table record when associating the first block of input with the first domain.

20. The computer program product of claim 15, where the front-end program comprises a natural-language processing technology configured to infer semantic meaning from natural-language user input submitted to the expert system through the front-end program, where the first block of input comprises natural-language text or speech, where the first chat-table record was created by the front-end program upon receipt by the front-end program of the first block of input, where the first chat-table record identifies characteristics of the first block of input, and where the characteristics comprise:
an identifier of the user session,
a time stamp that identifies when the first block of input was received, and
the first semantic meaning.

* * * * *